United States Patent [19]

Grenner

[11] Patent Number: 4,906,439
[45] Date of Patent: Mar. 6, 1990

[54] BIOLOGICAL DIAGNOSTIC DEVICE AND METHOD OF USE

[75] Inventor: Gerd Grenner, Lincoln, Mass.

[73] Assignee: PB Diagnostic Systems, Inc., Westwood, Mass.

[21] Appl. No.: 133,071

[22] Filed: Dec. 21, 1987

Related U.S. Application Data

[63] Continuation-in-part of Ser. No. 843,766, Mar. 25, 1986, abandoned.

[51] Int. Cl.⁴ .................... G01N 21/77; G01N 33/52
[52] U.S. Cl. ........................ 422/56; 422/55; 422/58; 422/100; 422/101; 435/805; 436/165; 436/169; 436/170; 436/177; 436/180; 436/518; 436/524; 436/531; 436/175
[58] Field of Search .............. 422/55, 56, 57, 58, 422/61, 100, 101, 102; 435/805; 436/169, 170, 165, 175, 177, 178, 180, 518, 524, 531

[56] References Cited

U.S. PATENT DOCUMENTS

| | | | |
|---|---|---|---|
| 3,216,804 | 11/1965 | Natelson | 23/253 |
| 3,607,093 | 9/1971 | Stone | 23/253 |
| 3,723,064 | 7/1971 | Liotta | 23/230 R |
| 4,233,029 | 11/1980 | Columbus | 23/230 R |
| 4,256,693 | 3/1981 | Kondo et al. | 422/56 |
| 4,292,272 | 9/1981 | Kitajima et al. | 422/57 |
| 4,323,536 | 4/1982 | Columbus | 422/56 |
| 4,426,451 | 1/1984 | Columbus | 436/518 |
| 4,477,575 | 10/1984 | Vogel et al. | 436/170 |

FOREIGN PATENT DOCUMENTS

0051183  5/1982  European Pat. Off. .
0160916 11/1985  European Pat. Off. .

Primary Examiner—Robert J. Hill, Jr.
Attorney, Agent, or Firm—Gaetano D. Maccarone

[57] ABSTRACT

A biological diagnostic device and process for efficiently and accurately analyzing a sample of a biological fluid for in analyte of interest. The device, which is a preferred embodiment utilized for the analysis of whole blood samples, comprises a diagnostic test element and a sample application unit comprising a fluid delivery element and means for providing sample fluid to the fluid delivery element. The fluid delivery element comprises a layer having a plurality of grooves, or channels, in the surface thereof which is adjacent the test element. The fluid which is provided to the grooves is subsequently delivered to the test element.

14 Claims, 3 Drawing Sheets

BIOLOGICAL DIAGNOSTIC DEVICE AND METHOD OF USE

CROSS-REFERENCE TO RELATED APPLICATIONS

This is a continuation-in-part application of prior copending application of Ser. No. 843,766, filed Mar. 25, 1986, now abandoned.

BACKGROUND OF THE INVENTION

Assay elements for the rapid analysis of analytes present in biological fluids are known in the art. In one type of such assay elements the sample fluid, e.g., plasma or serum, is applied to the element and the fluid, which contains the analyte of interest, then migrates to a reagent layer or layers. As a result of the interaction between the analyte and the reagent(s) present, a detectable change is brought about in the element which corresponds to the analyte of interest. The detectable change can be a color change which may be evaluated visually or read spectrophotometrically such as with a densitometer. In another scheme based on the presence of fluorescent labelled biological species a fluorescent output signal can be generated and read spectrofluorometrically. In order to obtain accurate and reproducible results with machine readable diagnostic devices it is essential that the plasma or serum be distributed uniformly throughout the assay element so that a uniform signal or color is provided for reading by the instrument.

Various techniques for accomplishing the uniform distribution of the plasma have been suggested in the art. U.S. Pat. No. 3,216,804 discloses an automatic chemical analyzer and sample dispenser and teaches that a uniform sample spot may be obtained by applying a drop of the sample on a filter paper which has fibers extending randomly in all directions or by using porous tapes or membranes. U.S. Pat. No. 3,607,093 discloses a device for testing biological fluids which comprises a liquid permeable membrane of uniform chemical composition which has substantially uniform porosity throughout. U.S. Pat. No. 3,723,064 discloses a multilayer device which has a sample receiving layer having uniform porosity which allows capillary migration to provide an even distribution of the components in the fluid. In cases where an incubation period is required, evaporation from the sample receiving layer could occur with a resultant change in the concentration of analyte in the sample.

U.S. Pat. No. 4,323,536 discloses test devices wherein sample fluid is conveyed to a plurality of test elements by a liquid capillary transport zone. The device comprises a first member, a second covering member, the members having opposing surfaces, and means for spacing the members apart a distance effective to induce capillary flow of liquid introduced between the surfaces and thus create a liquid transport zone. Portions of one or both surfaces may have a plurality of exposed grooves in order to control the liquid flow paths.

Of particular interest among rapid analytical elements are those which are capable of performing the analysis on samples of whole blood since these avoid the need for prior separation of blood cells from plasma such as by centrifuging. In such elements the sample, e.g., a drop of whole blood, is applied to the element which includes some means for separating the cells (erythrocytes, leucocytes) from the plasma and the plasma is then distributed uniformly to a reagent layer or layers so that a uniform signal or color is provided for reading by the instrument.

The known techniques for filtering a whole blood sample and uniformly distributing the plasma have not been entirely satisfactory. In addition to the separation and distribution functions the sample application layer must satisfy a number of other requirements. For example, there must not be any significant amount of binding of the analytes and reagents to the material in the sample application layer, the plasma-analyte concentration level must not be affected, there should be no lysis of the blood cells and the layer must provide a metered amount of plasma to the underlying reagent layers. The known sample application layers and materials fail to provide one or more of these requisite functions.

In an effort to obtain a satisfactory sample application scheme it has been suggested to divide the filtering and distribution functions between different materials. U.S. Pat. No. 4,477,575 discloses a technique for separating cells from plasma or serum which involves applying a sample of whole blood to a layer of glass fibers having an average diameter of 0.2 to 5 microns and a density of 0.1 to 0.5 g/cm³. There are also disclosed various biological diagnostic devices which incorporate such a glass fiber layer. In one embodiment (see, for example, FIG. 11) the plasma or serum which passes through the filter layer is taken up by a layer of an absorbent material such as cellulose paper or a synthetic fiber fleece which is in contact with the reaction layer. Due to capillary forces the plasma or serum is passed into the reaction layer where the detection reaction takes place.

This arrangement is not satisfactory in all instances. For example, it is not suitable for use with thin film multilayer diagnostic test elements. In such thin film multilayer elements the volume of fluid which is supplied to the test element must be very small and very precisely metered. Since the paper or fiber fleece is relatively thick and has a relatively large surface area the volume of fluid supplied to the test element is relatively large and the precision with which the amount of fluid can be controlled is relatively lower. In addition, because of the area of the relatively thick absorbent material it may give rise to relatively high levels of nonspecific binding of the analyte.

European Patent Application No. 0 160 916 discloses, in an analytical element, a volume filtration layer consisting of a fibrous material and a spreading layer having a liquid retaining capacity which is larger than that of the volume filtration layer. The spreading layer may be a fibrous material, woven cloth, knitted cloth or a non-fibrous porous medium. This arrangement suffers from various of the disadvantages previously discussed. For example, when the spreading layer is a non-fibrous membrane filter the pores of the membrane material are very small and fluid will not pass through easily without the application of pressure.

Accordingly, there is a continuing need for biological diagnostic devices having sample application units which can provide a uniform distribution of plasma or serum to the test element and, in addition, optionally can remove from the sample fluid any components which could interfere with the assay to be performed.

SUMMARY OF THE INVENTION

It is therefore an object of this invention to provide a novel biological diagnostic system.

It is another object of the invention to provide a diagnostic device which includes a diagnostic test element, a fluid delivery element and means for providing sample fluid to the delivery element.

It is still another object to provide a diagnostic device wherein the fluid delivery element comprises a layer which has a plurality of grooves in the surface thereof which is adjacent the test element.

It is a further object to provide a diagnostic device wherein the means for providing sample fluid to the fluid delivery element is a filter element which is capable of separating cells from plasma or serum.

Yet another object is to provide a diagnostic device which is adapted to be used with samples of whole blood.

Still another object is to provide a process for analyzing for an analyte of interest in a sample of a biological fluid.

BRIEF SUMMARY OF THE INVENTION

These and other objects and advantages are accomplished in accordance with the invention by providing a biological diagnostic device for rapidly, efficiently and accurately analyzing a biological fluid. The diagnostic device comprises a diagnostic test element and a sample application unit comprising a fluid delivery element and means for providing sample fluid to the fluid delivery element. The fluid delivery element comprises a layer which includes a plurality of grooves, or channels, in a surface thereof for delivery of fluid to the diagnostic test element which is arranged adjacent, and preferably in contact with, the grooved surface. The fluid sample may be provided to the fluid delivery element in various ways. Any means suitable for receiving a sample of a biological fluid and providing the fluid to the fluid delivery element may be utilized. In one embodiment a separate element such as a filter element or an absorbent material can be arranged in fluid contact with the grooves. In another embodiment the fluid supplying means may be combined in the same layer as the fluid delivery grooves. The particular technique used in any instance will be dependent in part upon the type of biological fluid to be analyzed. For example, where whole blood samples are involved it will be necessary to utilize a filter element capable of removing from the sample any components which could interfere with the analysis.

In operation a sample of the biological fluid is applied to the device and the fluid is subsequently brought by the grooves of the fluid delivery element to the diagnostic test element where it is imbibed into that element. In this manner there is obtained a uniform distribution of the fluid throughout the area of the test element surface which will be analyzed. It should be noted here that the detectable change in the test element, whether it is a color change which is to be evaluated visually or read out spectrophotometrically or whether it is some other type of change such as the generation of a fluorescent output signal which is to be read out spectrofluorometrically, will be analyzed over a specific portion of the test element surface typically a circular or rectangular area in the center of the test element. Thus, it is essential to obtain a uniform distribution of the test fluid throughout the area of the test element which will be analyzed.

In a preferred embodiment the diagnostic test element is a thin film multilayer test element. The sample delivery element is particularly well suited for use with thin film multilayer diagnostic test elements because the volume in the grooves can be made very small and controlled very precisely. For thin film multilayer diagnostic test elements it is necessary to deliver a relatively small volume of fluid to the test element. To ensure that the test element receives a volume of fluid equivalent to its wet uptake capacity, the fluid delivery system typically should be capable of delivering from about 110% to about 200% of the wet uptake volume of the test element. This requirement can be met by the grooved delivery element because as noted above, the volume of the grooves can be made relatively small. Accordingly, the delivery element is capable of providing, as is required with thin film multilayer test elements, a small volume of precisely metered sample fluid. A further advantage of the biological diagnostic device of the invention is that the sample fluid which is applied to the device is not exposed to the ambient environment very much, or at all, prior to being delivered to the diagnostic test element. Thus, any evaporation of any significance which could lead to a change in the analyte concentration is prevented.

BRIEF DESCRIPTION OF THE DRAWINGS

For a better understanding of the invention as well as other objects and further features thereof, reference is made to the following detailed description of various preferred embodiments thereof taken in conjunction with the accompanying drawings wherein.

DESCRIPTION OF THE PREFERRED EMBODIMENTS

Figure 1:
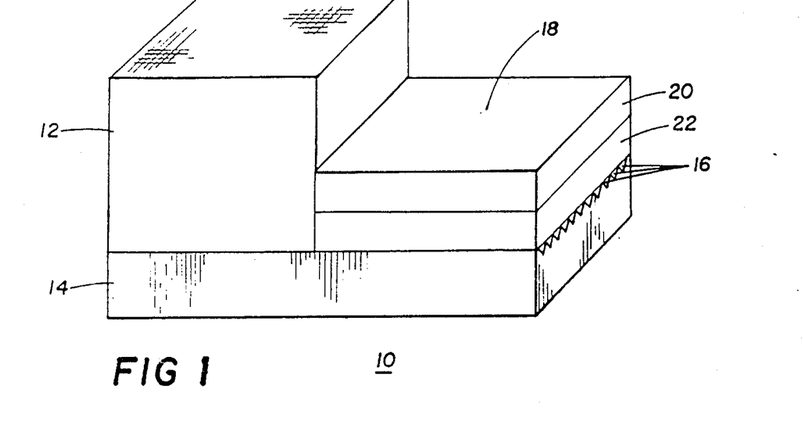
FIG. 1 is a partially schematic, perspective view of one embodiment of a diagnostic device according to the invention.

Referring to FIG. 1 there is seen a preferred embodiment of a diagnostic element 10 according to the invention. It should be recognized that the thickness of the device has been magnified for ease of illustration; the actual preferred devices of the invention are relatively thin, having typical thicknesses in the range of from about 1 mm to about 3 mm. The diagnostic device 10 comprises a filter element 12, a fluid delivery element 14 having a plurality of grooves 16 in the surface thereof which is adjacent the filter element and the diagnostic test element generally designated 18.

The filter element 12 may be any suitable material, synthetic or naturally occurring or a mixture of each type, which is capable of removing from the fluid sample any component(s) which could interfere with the analysis and which is inert to the analyte(s) of interest, that is, will not prevent any significant amount of said analyte(s) from passing through the filter element whether because of adsorption, reaction or otherwise. As shown the filter element is a flat, sheet-like layer; however, the element may be provided in any desired shape or configuration such as a pad or a curved layer. The type of filter material employed in the device is dependent upon the type of biological fluid to be analyzed. For example, a microporous filter element may be used to remove bacteria cells or microorganisms from the sample fluid. In a preferred embodiment wherein the sample is whole blood the filter element comprises fibrous material which is capable of separating cells such as, for example, erythrocytes, leucocytes, etc. from plasma or serum. Typical suitable fibrous materials include glass, quartz, cellulose acetate, cellulose, synthetic polymer fibers, such as polyamides or polyesters, and the like. In a preferred embodiment the fibrous material may be treated with a material such as gelatin, either inert or deionized, or serum albumin to substantially reduce or eliminate any binding thereto by an analyte of interest. The fibrous filter element typically has an average thickness of from about 0.5 mm to about 2.0 mm. The filter element 12 may be impregnated with a material which is capable of removing specific components from the fluid sample, for example, lipoproteins. Titanium dioxide is suitable for this purpose. Antibodies specific to components in the fluid may also be used.

The fluid delivery element 14 may comprise a sheet of any suitable material, transparent or opaque, including synthetic, film-forming polymeric materials, e.g., polyvinylacetate, polyvinylchloride, polyvinylchloride-polyvinylalcohol copolymers, polypropylene, polystyrene, cellulose acetate butyrate, hydrolyzed cellulose acetate butyrate and the like; metals, ceramics, etc. The material should be nonabsorbent or substantially nonabsorbent with respect to the fluid or any of the components thereof. In a preferred embodiment the grooved surface of the delivery element is treated such as by hydrolysis or with a material which causes its surface to be more easily wetted by the fluid. Consequently the fluid can be delivered more rapidly to the test element. Proteins such as gelatins and albumins as well as surfactants are suitable for this purpose. Some metals and polymeric materials strongly absorb proteins and the contact angles of fluids applied thereto are changed significantly. As noted above, the volume of the grooves can be relatively small. The small surface of the fluid delivery element is advantageous since any nonspecific binding of the analyte of interest to the delivery element is thereby minimized. Hydrolyzed cellulose acetate butyrate is a preferred material for the fluid delivery element because it is highly wettable. In a preferred embodiment the fluid delivery element comprises a clear polymeric material which allows an output signal, such as a spectrophotometric signal, to be read out through th delivery element. The thickness of the fluid delivery element is typically about 1 mm.

Figure 2:
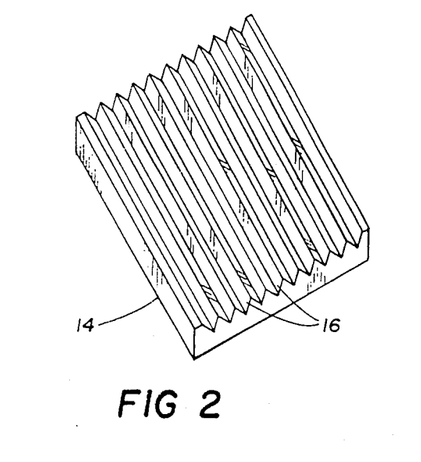
FIG. 2 is a partially schematic perspective view of a fluid delivery element.

The grooves 16 in the fluid delivery element may be of any shape such as, for example, convex, concave, v-shaped or rectangular. The rectangular shaped grooves include those which are relatively wide and which are separated by relatively thin walls. FIG. 2 illustrates a delivery element wherein the grooves have a triangular shape. The number of grooves in the element is typically from about 4 to about 50 per cm. The groove depth is typically from about 0.025 to about 0.2 mm and preferably from about 0.05 to about 0.160 mm. The groove depth, number of grooves and the dimensions of the delivery element are dependent principally upon the amount of sample which is to be delivered to the diagnostic test element. For a device intended for use with whole blood samples, the groove depth is typically from about 0.1 to about 0.125 mm and typically the fluid delivery element includes from about 20 to about 40 grooves per cm with a void volume of from about 5–10 $\mu l/cm^2$.

Figure 3:
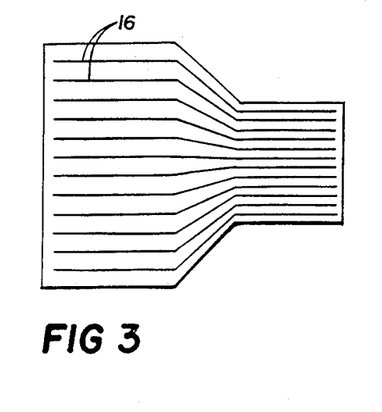
FIG. 3 is a partially schematic, top view of one embodiment of a fluid delivery element.

The grooves may be parallel to each other and have uniform width and depth as illustrated in FIG. 2. In other embodiments the grooves may not be parallel to each other and the depth and/or the width may not be the same along their length. FIG. 3 illustrates a delivery element for a diagnostic device wherein the filter element is larger than the diagnostic test element. As can be seen some of the grooves 16 would be configured differently from the others to permit collection of the fluid passing through the filter element and delivery to the test element. Further, the grooves could be arranged in various shapes such as curvilinear, concentric, etc. The grooves can be made by various techniques such as embossing, laser etching, etc.

The diagnostic test element 18 as shown comprises a thin film multilayer structure with a support layer 20 and reagent layer 22. A typical thin film test element has a thickness of from about 0.1 mm to about 0.3 mm. The diagnostic device may incorporate any diagnostic test element whether a single layer or multilayer. The test element 18 may be deposited on the grooved surface of the fluid delivery element such as by pressing it into contact or it can be adhered around its periphery to the delivery element with an adhesive material. The test element may be in contact with the filter element 12 as shown or it may be spaced apart from it. Where the filter and test elements are in contact with each other a thin film of a barrier material may be disposed at their interface to prevent any fluid from being drawn directly into the test element from the filter.

The diagnostic test elements which are useful in the diagnostic device of the invention are typically swellable when wet with fluid and the rate of swelling should be the same for a particular assay in all instances so as to give accurate, reproducible results. The pressure of the test element on the surface of the fluid delivery element may affect the rate of swelling of the former. In addition, the swelling of the test element may affect the rate at which the fluid is delivered to it. Accordingly, the groove shape and depth and the number of grooves in the fluid delivery element should be selected so as to ensure that the grooves are not filled by the swelled surface of the test element to the extent that the rate of delivery of the fluid is significantly altered or that the delivery of the fluid is prevented. An inert, nonswellable porous layer may be included between the fluid delivery and assay elements to prevent blockage of the grooves by the swelled surface of the assay element. The inert, nonswellable porous layer may be provided as an integral part of the assay element or the fluid delivery element or as a discrete layer arranged between the two elements. A suitable porous layer comprises a layer of particulate material.

As noted previously, the delivery element 14 may be transparent or opaque. Further, after the reaction is completed the test element may be analyzed visually or by an instrument and this may be done while the test element remains as an integral part of the diagnostic device or it may be detached from the device for this purpose. In a preferred embodiment the device is read out spectrophotometrically or spectrofluorometrically with the test element included. Thus, in this case, either the fluid delivery element or the base of the test element or both would be transparent.

Figure 4:
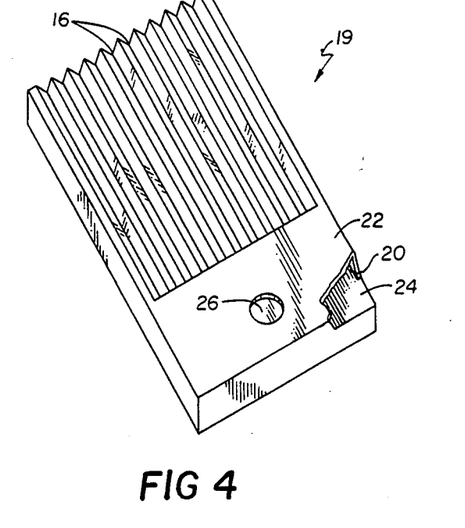
FIG. 4 is a partially schematic, perspective view of a sample application unit according to the invention.

FIG. 4 illustrates a preferred embodiment of the invention wherein the fluid delivery grooves and the means for providing sample fluid to the grooves are arranged in the same layer 19. In this embodiment there is provided in layer 19 a void area 20 which includes a top surface 22 and a bottom surface 24. The top surface 22 includes an aperture 26 for applying a sample fluid into void area 20. The top surface 22 and bottom surface 24 are spaced apart a capillary distance such that the sample fluid which is introduced into the void area 20 is drawn into the fluid delivery grooves by capillary action. The bottom surface 24 of void area 20 can be substantially coplanar with the bottom of the grooves or it may be slightly higher. Of course it is apparent that the grooves 16 in FIG. 4 would be covered with a diagnostic test element as shown in FIG. 1.

Although the void area 20 is illustrated in FIG. 4 with a top surface 22 having an aperture 26, the introduction of sample liquid into void area 20 and the generation of the capillary forces necessary to cause the liquid to be drawn into the grooves may be accomplished in various ways. For example, instead of top surface 22, a filter element or an absorbent material may be arranged over the void area 20. In this embodiment the sample fluid is applied to the filter or absorbent material and the fluid passes through these elements and flows into the void area 20. In essence the bottom surface of the filter or the absorbent material is arranged so as to be a capillary distance from bottom surface 24 of void area 20.

Figure 5:
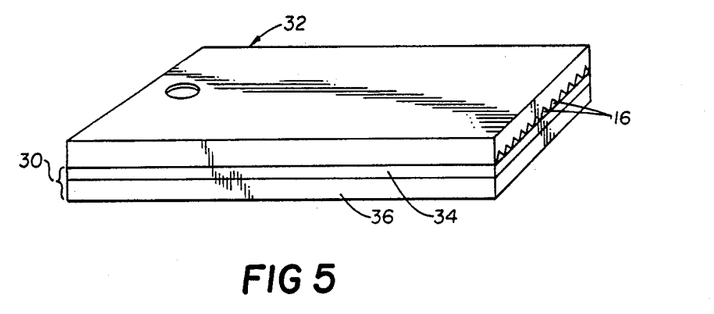
FIG. 5 is a partially schematic perspective view of a diagnostic device according to the invention.

FIG. 5 illustrates another embodiment of the diagnostic assay device of the invention wherein the grooves 16 are above the assay element, generally designated 30. In this embodiment the fluid delivery element 32 is arranged on the top surface of assay element 30. As is illustrated in FIG. 4 a void area is provided in layer 32 which includes a top surface with an aperture and a bottom surface spaced apart a capillary distance. The sample fluid is introduced through the aperture and drawn into the grooves by capillary forces. The assay element 30 may be any of those previously described. As shown the test element 30 comprises a reagent layer 34 and a support 36. In a particularly preferred embodiment the support layer 36 is transparent and the signal obtained may be read out spectrometrically or spectrofluorometrically through the support. It should also be noted here that the sample fluid may be introduced into the void area by other techniques such as those described in relation to FIG. 4.

Figure 6:
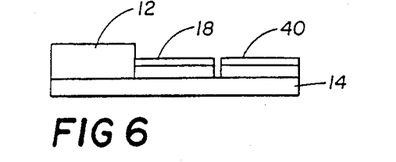
FIG. 6 is a partially schematic, cross-sectional view of another embodiment of a diagnostic device according to the invention.
Figure 7:
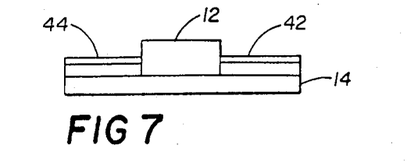
FIG. 7 is a partially schematic, cross-sectional view of another embodiment of a diagnostic device according to the invention.
Figure 8:
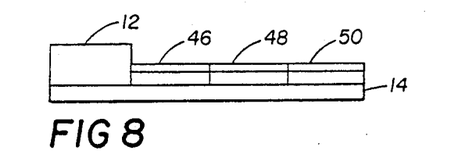
FIG. 8 is a partially schematic, cross-sectional view of another embodiment of a diagnostic device according to the invention.
Figure 9:
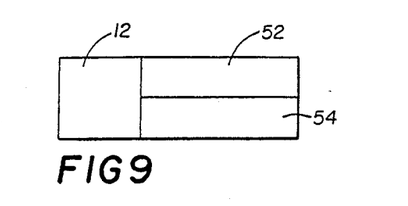
FIG. 9 is a partially schematic, top view of another embodiment of a diagnostic device according to the invention.

In another preferred embodiment illustrated in FIG. 6 a reagent blank element 40 is included in the diagnostic device. In a diagnostic element wherein the concentration of the desired analyte is determined by measuring a fluorescent output signal the reagent blank could test the fluorescence of the other materials present in the test element. In another embodiment a plurality of biological diagnostic test elements are disposed on the plasma or serum delivery element with each test element measuring the concentration of a different analyte present in the sample. The additional test elements or the reagent blank can be located in contact with or spaced apart from diagnostic test element 18 or they may be disposed on the other side of the filter element 12. FIG. 7 illustrates a diagnostic device wherein test elements 18 and 44 respectively are located on opposite sides of the filter element 12. FIG. 8 illustrates a diagnostic device having three diagnostic test elements 46, 48 and 50. FIG. 9 illustrates a diagnostic device wherein diagnostic test elements 52 and 54 respectively are arranged on the fluid delivery element in side by side fashion.

Figure 10:
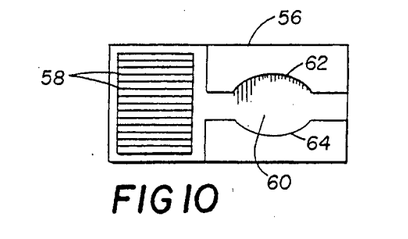
FIG. 10 is a partially schematic top view of one embodiment of a fluid delivery element according to the invention.

FIG. 10 illustrates a fluid delivery element, generally designated 56, having a plurality of grooves 58 arranged in the surface area generally underlying the filter element. The area of the delivery element, generally designated 60 which commences at the point where the grooves terminate and which is bounded by lines 62 and 64, represents a void area. The void area 60 may have a depth approximately equal to the depth of the grooves 58 or the respective depths may be different. The circular portion of the void area represents the area of the test element where the detectable change will be viewed or measured. In a diagnostic test device adapted for use with samples of whole blood the grooves and the void area typically have a depth of about 0.125 mm and the diameter of the circular portion of the void area 60 typically is about 10 mm.

Figure 11:
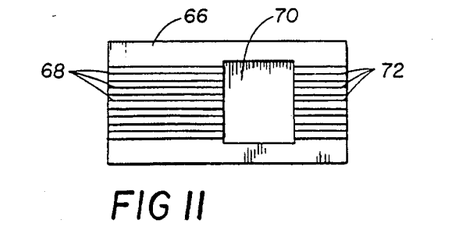
FIG. 11 is a partially schematic top view of another embodiment of a fluid delivery element according to the invention.

FIG. 11 illustrates another fluid delivery element, generally designated 66 having a plurality of grooves 68 arranged in the surface area generally underlying the filter element. The area of the delivery element, generally designated 70, represents a void area which, as is the case with the void area 60 in FIG. 10 may have a depth approximately equal to, or different than, that of the grooves 68. The square part of the void area represents the area of the test element where the detectable change will be viewed or measured. The delivery element further includes grooves 66 on the other side of the void area to assist in the flow of the fluid to the test element.

In commercial use the diagnostic test devices of the invention typically would be used with an automated test apparatus which would perform the analysis automatically and record the result. In such a test apparatus the diagnostic test device would typically be mounted in a holder which could be an integral part of the apparatus.

The invention will now be described further in detail with respect to specific preferred embodiments by way of examples it being understood that these are intended to be illustrative only and the invention is not limited to the materials, conditions, process parameters, etc., which are recited therein.

EXAMPLE 1

An experiment was conducted using 8 square filter pads of three different glass fiber materials and a clear plastic delivery element having approximately 21 convex, 0.16 mm deep, grooves per cm. The filter pad was placed at one end of the grooved surface of the delivery element and the remainder of the delivery element was covered with a 9×75 mm clear layer of polyester film base so the delivery element could be observed visually. A sample of whole blood was dropped onto the filter pad and the times required for the pad to fill were recorded. In addition the amount of plasma which was separated from the sample and entered the grooves of the delivery element was calculated. The grooves were measured to hold a volume of 5.8 µl/cm².

The experiment was conducted with glass fibers that were untreated; those which had been treated with deionized gelatin (having 12 ppm of calcium); and with those which had been treated with deionized gelatin and Tween 20, a surfactant available from Rohm and Haas Co. The glass fibers were treated with deionized gelatin by imbibing a 1% aqueous gelatin solution into the filter pad and subsequently washing three times with water. Where the glass fibers were also treated with Tween 20 in addition to gelatin, the first washing step was carried out with a 1% aqueous solution of Tween 20 followed by two washes with water.

50 µg insulin/l plasma

A sample containing the analyte in mixed plasma was applied to an 0.8 cm diameter filter pad and allowed to incubate for 10 minutes at room temperature. The void volume for each filter pad was determined and the sample applied was equal to the void volume. For the Sartorius 13430 filter pad the sample was 90 µl; for the Whatman GF/B it was 65 µl; and for the Whatman QM-A, 45 µl. After the incubation period the filter pad was washed twice with 1 ml volumes of saline solution. Subsequently the radioactivity of the filter pad was measured and the percentage of nonspecific binding of the analyte was calculated.

The three types of glass fibers exhibited low nonspecific binding to the analytes: 2.6% of digoxin and 6.0% of insulin, respectively, were bound to the untreated Whatman GF/B filter material and 2.9% of digoxin and 6.2% of insulin, respectively were bound to the Whatman QM-A filter material. The percentage of nonspeci-

| FILTER (treatment) | BLOOD VOL. [µl] | PAD FILLING TIME* [sec] | PLASMA YIELD* [µl] | OBSERVATIONS | |
|---|---|---|---|---|---|
| Sartorius 13430 | | | | | |
| (None) | 100 | 150 | 2 | + | |
|  | 110 | 165 | 13.5 | + | + |
|  | 120 | 93 | 19.7 | − | + |
| (Gelatin) | 100 | 105 | 7 | + | + |
|  | 110 | 68 | 15.5 | − | + |
|  | 120 | 60 | 22.5 | − | − |
| (Gelatin/Tween) | 100 | 20 | 4 | − | + |
|  | 110 | 10 | 10 | + | − |
|  | 120 | 10 | 22 | − | − |
| Whatman QM-A | | | | | |
| (None) | 60 | 25 | 14.5 | + | + |
|  | 70 | 20 | 22 | − | + |
|  | 80 | 18 | 29.5 | | |
| (Gelatin) | 60 | 17.5 | 10 | − | − |
|  | 70 | 20 | 24 | − | − |
|  | 80 | 17.5 | 30.5 | − | − |
| (Gelatin/Tween) | 60 | 17.5 | 15.5 | + | + |
|  | 70 | 12.5 | 25 | − | − |
|  | 80 | 10 | 29.5 | − | − |
| Whatman GF/B | | | | | |
| (None) | 80 | 210 | 4 | + | + |
|  | 90 | 250 | 8 | − | + |
|  | 100 | 270 | 8 | + | + |
| (Gelatin) | 80 | 120 | 10 | | + |
|  | 90 | 97.5 | 9.5 | + | + |
|  | 100 | 65 | 13.5 | + | + |
| (Gelatin/Tween) | 80 | 150 | 5 | + | + |
|  | 90 | 95 | 10.5 | + | + |
|  | 100 | 70 | 23.5 | + | + |

*values are average of two determinations unless otherwise indicated by number of observations.
+ indicates clear plasma in the grooves.
− indicates some erythrocytes were observed in at least one groove.

It can be seen that the filter pads were generally effective in separating the plasma from the erythrocytes in the sample.

EXAMPLE II

An experiment was conducted to determine the extent of binding of four analytes, namely digoxin, hCG theophylline and insulin, to various glass fibers. The experiment was conducted with untreated glass fibers and those which had been treated with deionized gelatin and Tween 20. The filter treatments were carried out as described in Example I.

The analytes were labelled with Iodine - 125 and their concentrations in the plasma samples were:

7.81 µg digoxin/l plasma
1 I.U. hCG/l plasma
1.8 mg theophylline/l plasma fic binding of the other analyte/filter combinations was less than 1%. Further, for the Whatman glass fiber materials it was found that treatment with deionized gelatin and Tween 20 reduced the nonspecific binding of digoxin and insulin to less than 1%.

EXAMPLE III

An experiment was conducted to determine the precision of fluid uptake for a test element of a diagnostic device according to the invention. The experiment was conducted with 7×7 mm square filter pads of two different glass fiber materials and a fluid delivery element having 32 convex, 0.125 mm deep grooves per cm. The filter pad was placed on one end of the grooved surface of the delivery element and a 7×7 mm square test element covered part of the remaining surface of the delivery element. The test element comprised a clear polystyrene base coated with an 18 g/m² agarose layer with the agarose layer in contact with the grooved surface of the fluid delivery element.

A sample of whole blood or plasma which was derived from the same blood sample by centrifugation was applied to the filter pad. After three minutes the test element was removed from the delivery element and tested for the uptake of fluid by weighing it.

The experiment was conducted with two different glass fiber filters which were treated with gelatin and Tween 20 as described in Example 1.

| FILTER | SAMPLE | VOL. [μl] | NO. OF EXP. | FLUID UPTAKE* [mg/cm²] |
|---|---|---|---|---|
| Sartorius 13430 | Whole Blood | 90 | 8 | 4.66 ± 0.08 |
| Sartorius 13430 | Plasma | 90 | 8 | 4.66 ± 0.18 |
| Whatman QM-A | Whole Blood | 50 | 8 | 4.40 ± 0.12 |
| Whatman QM-A | Plasma | 50 | 8 | 4.58 ± 0.12 |

*mean value and standard deviation of 8 determinations

It can be seen that the fluid uptake of the test element was very precise for both the whole blood and plasma samples. Further, the fluid uptake of the Sartorius 13430 filter was the same for the whole blood and plasma samples and virtually the same with the Whatman QM-A filter.

Although the invention has been described with respect to various embodiments thereof, it is not intended to be limited thereto but rather those skilled in the art will recognize that variations and modifications may be made therein which are within the spirit of the invention and the scope of the appended claims.

What is claimed is:

1. A biological diagnostic device comprising
   a sample application unit including a fluid delivery element with a plurality of grooves in a surface thereof for providing a path for fluids to flow therealong and
   means for providing fluid to said grooves arranged in fluid contact with said grooves; and
   at least one diagnostic test element arranged in contact with said grooves to receive fluid admitted to said grooves from said fluid providing means.

2. The diagnostic device as defined in claim 1 wherein said fluid providing means comprises a filter element.

3. The diagnostic device as defined in claim 2 wherein said filter element comprises a layer of fibrous material and is capable of separating cells from plasma or serum.

4. The diagnostic device as defined in claim 3 wherein said diagnostic test element is a multilayer immunoassay element.

5. The diagnostic device as defined in claim 3 wherein said fibrous filter material has been treated with deionized gelatin or albumin.

6. The diagnostic device as defined in claim 3 wherein said fibrous filter material has been treated with a surfactant.

7. The diagnostic device as defined in claim 3 wherein said fibrous filter material has been treated with a protein.

8. The diagnostic device as defined in claim 1 wherein said fluid delivery element includes from about 4 to about 50 grooves per cm, said grooves having a depth of from about 0.05 to about 0.160 mm.

9. The diagnostic device as defined in claim 8 wherein said fluid delivery element comprises a substantially transparent polymeric material.

10. The diagnostic device as defined in claim 9 wherein said fluid delivery element comprises hydrolyzed cellulose acetate butyrate.

11. The diagnostic device as defined in claim 1 wherein the device includes a plurality of diagnostic test elements, each of said diagnostic test elements being arranged in contact with said grooves to receive fluid admitted to said grooves from said fluid providing means.

12. A method for analyzing for an analyte of interest in a biological fluid comprising
    applying a sample of a biological fluid to a fluid delivery element having a plurality of grooves in a surface thereof for providing a path for said fluid to flow therealong;
    imbibing at least some of said fluid from said grooves into a diagnostic test element arranged in contact with said grooves; wherein a signal is generated by said test element as a function of an analyte present in said fluid; and detecting said signal.

13. The diagnostic method as defined in claim 12 wherein said diagnostic test element is a multilayer immunoassay element.

14. The diagnostic method as defined in claim 12 wherein said fluid delivery element comprises a substantially transparent material.

* * * * *

UNITED STATES PATENT AND TRADEMARK OFFICE
CERTIFICATE OF CORRECTION

PATENT NO. : 4,906,439

DATED : March 6, 1990

INVENTOR(S) : Gerd Grenner et al

It is certified that error appears in the above-identified patent and that said Letters Patent is hereby corrected as shown below:

On the title page, delete "Inventor" and insert --- Inventors ---; after "Gerd Grenner, Lincoln, Mass." insert --- Jurgen H. Hachmann, Frankfurt, Federal Republic of Germany, James J. Manning, Braintree, Mass., George O. Neely, Dayton, Ohio, Hans-Erwin Pauly, Buchenau, Federal Republic of Germany and Melitta Staedter, Malden, Mass. ---

Abstract, line 3, delete "in" and insert --- an ---; delete "is" and insert --- in ---.

Abstract, line 4, after "embodiment" insert --- is ---.

Column 5, line 67, delete "th" and insert --- the ---.

Column 8, line 11, delete "18" and insert --- 42 ---.

Signed and Sealed this

Sixteenth Day of October, 1990

Attest:

HARRY F. MANBECK, JR.

Attesting Officer

Commissioner of Patents and Trademarks